(12) United States Patent
Albert et al.

(10) Patent No.: US 6,642,225 B2
(45) Date of Patent: Nov. 4, 2003

(54) DIAZACYCLOALKANEDIONE DERIVATIVES

(75) Inventors: Rainer Albert, Basel (CH); Janet Dawson, Bennwil (CH); Claus Ehrhardt, Lorrach (DE); Sompong Wattanasin, Hopatcong, NJ (US); Gabriele Weitz-Schmidt, Bad-Krozingen (DE); Karl Welzenbach, Basel (CH)

(73) Assignee: Novartis AG, Basel (CH)

( * ) Notice: Subject to any disclaimer, the term of this patent is extended or adjusted under 35 U.S.C. 154(b) by 0 days.

(21) Appl. No.: 09/968,389

(22) Filed: Oct. 2, 2001

(65) Prior Publication Data

US 2002/0061878 A1 May 23, 2002

Related U.S. Application Data

(60) Provisional application No. 60/237,231, filed on Oct. 2, 2000.

(51) Int. Cl.[7] ............. C07D 241/00; C07D 243/00; C07D 401/00; C07D 403/00; A61K 31/495
(52) U.S. Cl. ........... 514/218; 514/252.13; 514/253.01; 514/253.02; 514/253.04; 514/255.02; 540/492; 544/359; 544/360; 544/361; 544/362; 544/363; 544/385
(58) Field of Search ................. 544/359, 360, 544/361, 362, 363, 385; 514/252.13, 253.01, 253.02, 253.04, 255.02, 218; 540/492

(56) References Cited

U.S. PATENT DOCUMENTS

| | | | |
|---|---|---|---|
| 5,281,585 A | 1/1994 | Duggan et al. | 514/79 |
| 5,382,584 A | 1/1995 | Balasubramanian | 514/252 |
| 5,932,579 A | 8/1999 | Campbell et al. | 514/249 |
| 6,211,183 B1 | 4/2001 | Marlowe et al. | 514/255.02 |
| 6,399,599 B1 | 6/2002 | Albert et al. | 514/218 |

FOREIGN PATENT DOCUMENTS

| | | |
|---|---|---|
| EP | 0 008 186 A1 | 2/1980 |
| EP | 365 992 A1 | 5/1990 |
| WO | WO 92/07568 | 5/1992 |
| WO | WO 96/31214 | 10/1996 |
| WO | WO 97/40023 | 10/1997 |
| WO | WO 97/44329 | 11/1997 |
| WO | WO 97/48685 | 12/1997 |
| WO | WO 98/09987 | 3/1998 |
| WO | WO 98/46591 | 10/1998 |
| WO | WO 98/46626 | 10/1998 |
| WO | WO 98/46627 | 10/1998 |
| WO | WO 00/68188 | 11/2000 |
| WO | WO 01/27102 A1 | 4/2001 |

OTHER PUBLICATIONS

Gerona–Navarro et al., "Entry to New Conformationally Constrained Amino Acids. First Synthesis of 3–Unsubstituted 4–Alkyl–4–carboxy–2–azetidinone Derivatives via an Intramolecular $N^{\alpha}$–$C^{\alpha}$–Cyclization Strategy", J.Org.Chem., vol. 66, pp. 3538–3547 (2001).
Abstract (XP–002195149) of Document AR.
Callahan, J.F. et al., Tetrahedron, vol. 49, No. 17, pp. 3479–3488 (1993).
Taylor E.W. et al., Pharmaceutical Research, vol. 14, No. 5, pp. 572–577 (1997).
Onoyama K. et al., Clin. Pharmacol. Ther., vol. 43, No. 3, pp. 242–249 (1988).
Chemical Abstracts 1998:101407 CAPLUS.
Chemical Abstracts 1997:330708 CAPLUS.
Chemical Abstracts 1999:614098 CAPLUS.
Chemical Abstracts 1995:421551 CAPLUS.
Derwent Abstract 97–010414/01 (SU 1651527–A3).
Derwent Abstract 90–084261/12 (DE 3830–096–A).
Derwent Abstract 86–126570/20 (EP 181–152–A).
Derwent Abstract 86–179263/28 (J6 1112–060–A).
Derwent Abstract 15139C/09 (EP 8–186).
Derwent Abstract 91–310307/42 (WO 9114–378–A).

*Primary Examiner*—Bruck Kifle
(74) *Attorney, Agent, or Firm*—Norbert Gruenfeld

(57) ABSTRACT

Compounds of formula I

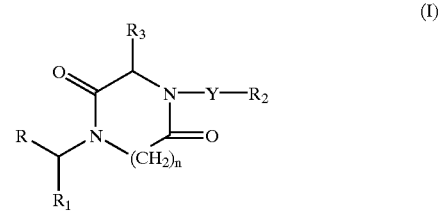

wherein R is carboxy, esterified carboxy or amidated carboxy;
  $R_1$ and $R_3$ are independently lower alkyl, (hydroxy, lower alkoxy, amino, acylamino, mono- or di-lower alkylamino or mercapto)-lower alkyl, lower alkyl-(thio, sulfinyl or sulfonyl)-lower alkyl, cycloalkyl, aryl, biaryl, (cycloalkyl, aryl or biaryl)-lower alkyl, or (carboxy, esterified carboxy or amidated carboxy)-lower alkyl;
  $R_2$ is hydrogen, lower alkyl, cycloalkyl, aryl, biaryl, arylaminocarbonyl, or aryl-(oxy, thio or amino);
  n is 1 or 2;
  Y is lower-alkylene or lower alkenylene;
and pharmaceutically acceptable salts thereof; which are useful as LFA-1 antagonists.

17 Claims, No Drawings

DIAZACYCLOALKANEDIONE DERIVATIVES

CROSS-REFERENCE TO RELATED APPLICATIONS

This application claims the benefit of provisional Application No. 60/237,231 filed Oct. 2, 2000, which is incorporated herein by reference.

BACKGROUND OF THE INVENTION

Lymphocyte function associated antigen 1 (LFA-1) mediates lymphocyte adhesion and plays a key role in inflammation and the immune response.

LFA-1 binds to intracellular adhesion molecules, e.g., ICAM-1, ICAM-2 or ICAM-3. The LFA-1/ICAM-1, ICAM-2 or ICAM-3 mediated interactions have been implicated in various disorders including transplant rejection, chronic inflammation, psoriasis, eczema/dermatitis, asthma and arthritis. LFA-1 antagonists are thus useful for the treatment and/or prevention of disorders which are responsive to LFA-1 inhibition, e.g., those cited herein, such as rheumatoid arthritis.

SUMMARY OF THE INVENTION

The present invention relates to diazacycloalkanedione derivatives, e.g., diazepanedione (hexahydrodiazepinedione) and diketopiperazine derivatives of formula I described herein which are particularly useful as LFA-1 antagonists, pharmaceutical compositions thereof, their methods of preparation and methods of treating conditions in mammals which are responsive to LFA-1 antagonism using said compounds or pharmaceutical compositions thereof.

DETAILED DESCRIPTION OF THE INVENTION

The invention relates particularly to compounds of formula I

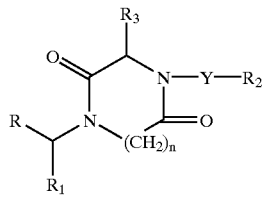

(I)

wherein R is carboxy, esterified carboxy or amidated carboxy;

$R_1$ and $R_3$ are independently lower alkyl, (hydroxy, lower alkoxy, amino, acylamino, mono- or di-lower alkylamino or mercapto)-lower alkyl, lower alkyl-(thio, sulfinyl or sulfonyl)-lower alkyl, cycloalkyl, aryl, biaryl, (cycloalkyl, aryl or biaryl)-lower alkyl, or (carboxy, esterified carboxy or amidated carboxy)-lower alkyl;

$R_2$ is hydrogen, lower alkyl, cycloalkyl, aryl, biaryl, arylaminocarbonyl, or aryl-(oxy, thio or amino); n is 1 or 2;

Y is lower-alkylene or lower alkenylene;
and pharmaceutically acceptable salts thereof.

A particular embodiment of the invention relates to the compounds of formula I wherein R is carboxy derivatized in form of a pharmaceutically acceptable amide; $R_1$ is aryl-lower alkyl; $R_2$ is aryl; $R_3$ is lower alkyl, aryl, or cycloalkyl-lower alkyl; and Y is $C_1$–$C_4$-alkylene or $C_{2-4}$-alkenylene; and pharmaceutically acceptable salts thereof.

A more particular embodiment of the invention relates to the compounds of formula II

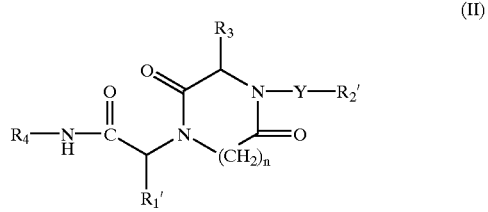

(II)

wherein $R_1'$ is bicyclic aryl-lower alkyl; $R_2'$ is bicyclic aryl; $R_3'$ is monocyclic aryl or lower alkyl; $R_4$ is hydrogen or lower alkyl; n is 1 or 2; Y is $C_{1-4}$-alkylene; and pharmaceutically acceptable salts thereof.

Particular embodiments of the invention relate to compounds of formula I and II wherein n is 1 and wherein n is 2.

Further preferred are said compound of formula II wherein $R_1'$ is naphthyl-lower alkyl or quinolinyl-lower alkyl; $R_2'$ is quinolinyl; $R_3'$ is isobutyl; Y is methylene, and n is 2; and pharmaceutically acceptable salts thereof.

Compounds of the invention may possess one or more asymmetric centers and can exist as diastereomers, racemates and the enantiomers thereof, all of which are within the purview of the invention.

Preferred are the diastereomers of the formula Ia or IIa

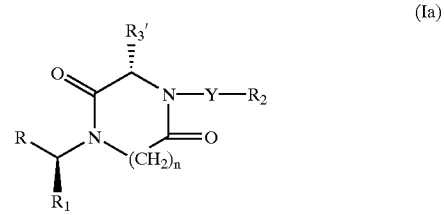

(Ia)

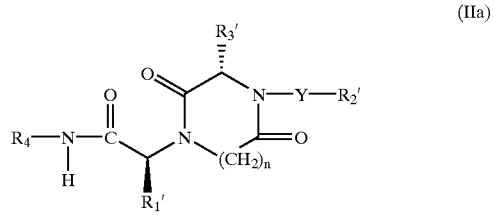

(IIa)

wherein n, Y, R, $R_1$, $R_2$ and $R_3$ in formula Ia, and n, Y, $R_1'$, $R_2'$, $R_3'$ and $R_4$ in formula IIa have meaning as defined above.

Unless otherwise indicated, the general definitions used herein have the following meaning within the scope of the present invention.

Aryl represents carbocyclic or heterocyclic aryl, either monocyclic or bicyclic.

Monocyclic carbocyclic aryl represents optionally substituted phenyl, being preferably phenyl or phenyl substituted by one to three substituents, such being advantageously lower alkyl, hydroxy, lower alkoxy, acyloxy, halogen, cyano, trifluoromethyl, carbocyclic aryloxy or carbocyclic aryl-lower alkoxy; or phenyl substituted on adjacent carbon atoms by lower alkylene or by lower alkylene interrupted by O, or S or by N optionally substituted by lower alkyl.

Bicyclic carbocyclic aryl represents 1- or 2-naphthyl or 1- or 2-naphthyl substituted by, e.g., lower alkyl, lower alkoxy or halogen, advantageously 2-naphthyl. Naphthyl may also be named naphthalenyl.

Monocyclic heterocyclic aryl represents, e.g., optionally substituted thiazolyl, thienyl, furanyl or pyridyl.

Optionally substituted furanyl represents 2- or 3-furanyl preferably substituted by lower alkyl.

Optionally substituted pyridyl represents 2-, 3- or 4-pyridyl or 2-, 3- or 4-pyridyl preferably substituted by lower alkyl, halogen or cyano.

Optionally substituted thienyl represents 2- or 3-thienyl or 2- or 3-thienyl preferably substituted by lower alkyl.

Optionally substituted thiazolyl represents, e.g., 2- or 4-thiazolyl, or 2- or 4-thiazolyl preferably substituted by lower alkyl.

Bicyclic heterocyclic aryl represents, e.g., quinolinyl, isoquinolinyl, indolyl or benzothiazolyl optionally substituted by hydroxy, lower alkyl, lower alkoxy or halogen. Indolyl may also bear a substituent attached to the ring nitrogen, e.g., lower alkyl or aryl-lower alkyl.

Aryl-lower alkyl is advantageously arylmethyl optionally substituted on phenyl by one or two of lower alkyl, lower alkoxy, hydroxy, lower alkanoyloxy, halogen, cyano or trifluoromethyl.

Biaryl represents phenyl substituted by carbocyclic aryl or heterocyclic aryl as defined herein, ortho, meta or para to the point of attachment of the phenyl ring, advantageously para, such as biphenyl, particularly 4-biphenyl, or pyridylphenyl, particularly 4-pyridylphenyl.

The term "lower" referred to herein in connection with organic radicals or compounds respectively defines such with up to and including 7, preferably up and including 4 and advantageously one or two carbon atoms. Such may be straight chain or branched.

A lower alkyl group preferably contains 1–4 carbon atoms and represents for example methyl, ethyl, propyl or butyl.

A lower alkylene group preferably contains 1–4 carbon atoms, and represents, for example, methylene, ethylene, propylene and the like.

A lower alkenylene group preferably contains 2–4 carbon atoms, and represents, for example, propenylene.

Cycloalkyl represents preferably cyclopentyl, cyclohexyl or cycloheptyl.

A lower alkoxy group preferably contains 1–4 carbon atoms and represents for example, methoxy, propoxy, isopropoxy or advantageously ethoxy.

Halogen (halo) preferably represents fluoro or chloro, but may also be bromo or iodo.

Acyl is derived from a carboxylic acid or carbonic acid and represents preferably optionally substituted lower alkanoyl, aroyl, lower alkoxycarbonyl or aryl-lower alkoxycarbonyl, advantageously aroyl.

Lower alkanoyl is preferably acetyl, propionyl, butyryl, or pivaloyl.

Optionally substituted lower alkanoyl for example represents lower alkanoyl or lower alkanoyl substituted, e.g., by lower alkoxycarbonyl, lower alkanoyloxy, lower alkanoylthio, lower alkoxy, or by lower alkylthio.

Aroyl is preferably monocyclic carbocyclic or monocyclic heterocyclic aroyl.

Monocyclic carbocyclic aroyl is preferably benzoyl or benzoyl substituted by lower alkyl, lower alkoxy, halogen or trifluoromethyl.

Monocyclic heterocyclic aroyl is preferably pyridylcarbonyl or thienylcarbonyl.

Acyloxy is preferably optionally substituted lower alkanoyloxy, lower alkoxycarbonyloxy, monocyclic carbocyclic aroyloxy or monocyclic heterocyclic aroyloxy.

Esterified carboxy represents carboxy derivatized in form of a pharmaceutically acceptable ester, preferably lower alkyl esters, cycloalkyl esters, lower alkenyl esters, benzyl esters, mono or disubstituted lower alkyl esters, e.g., the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxy-methyl ester, and the like conventionally used in the art.

Amidated carboxy represents carboxy derivatized in form of a pharmaceutically acceptable amide, e.g., primary, secondary and tertiary amides, e.g., the unsubstituted the N-mono-lower alkyl or N,N-di-lower alkylamides, or the amides of cyclic amines, e.g., of piperidine, pyrrolidine, morpholine or optionally substituted piperazine.

Pharmaceutically acceptable salts of acids of the invention are salts derived from pharmaceutically acceptable bases, e.g., alkali metal salts (e.g., sodium, potassium salts), alkaline earth metal salts (e.g., magnesium, calcium salts), amine salts (e.g., ethanolamine, diethanolamine, lysine and tromethamine salts) and the like conventionally used in the art.

Pharmaceutically acceptable salts of basic compounds of the invention are acid addition salts, e.g., of mineral acids, organic carboxylic acids, and organic sulfonic acids, e.g., hydrochloric acid, methanesulfonic acid, and the like.

The compounds of the invention of formula I can be prepared
(a) by cyclizing a compound of the formula III or a reactive functional derivative thereof

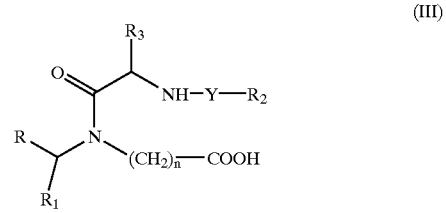

(III)

wherein R, $R_1$–$R_3$, Y and n have meaning as defined above; or
(b) by cyclizing a compound of the formula IV or a reactive functional derivative thereof

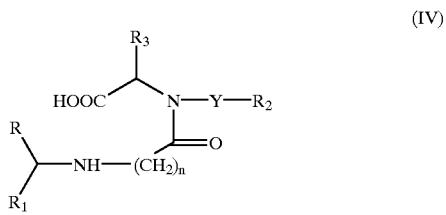

(IV)

wherein R, $R_1$–$R_3$, Y and n have meaning as defined above.

Abbreviations used throughout the application are those commonly used in the art, e.g.,
DCCI=Dicyclohexylcarbodiimide
DIPCI=Diisopropylcarbodiimide
HOBT=1-Hydroxybenzotriazole
NMM=N-methylmorpholine
DIEA=Diisopropylethylamine
HATU=O-(7-azabenzotriazol-1-yl)-1,1,3,3-tetramethyluronium hexafluorophosphate
r.t.=room temperature
TEA=Triethylamine
TFA=trifluoroacetic acid A reactive functional derivative of a compound of formula III or IV includes, e.g., a halide, ester or anhydride of the respective carboxylic acid.

The cyclization of an intermediate of the formula III or IV may be carried out according to methodology known in the art for formation of a lactam, e.g., using a condensing agent, such as HATU in the presence of diisopropylethylamine in a polar solvent, such as dimethylformamide.

Illustrative of the invention, the preparation of compounds of formula II wherein n is 1 can be carried out as illustrated below and in the examples herein.

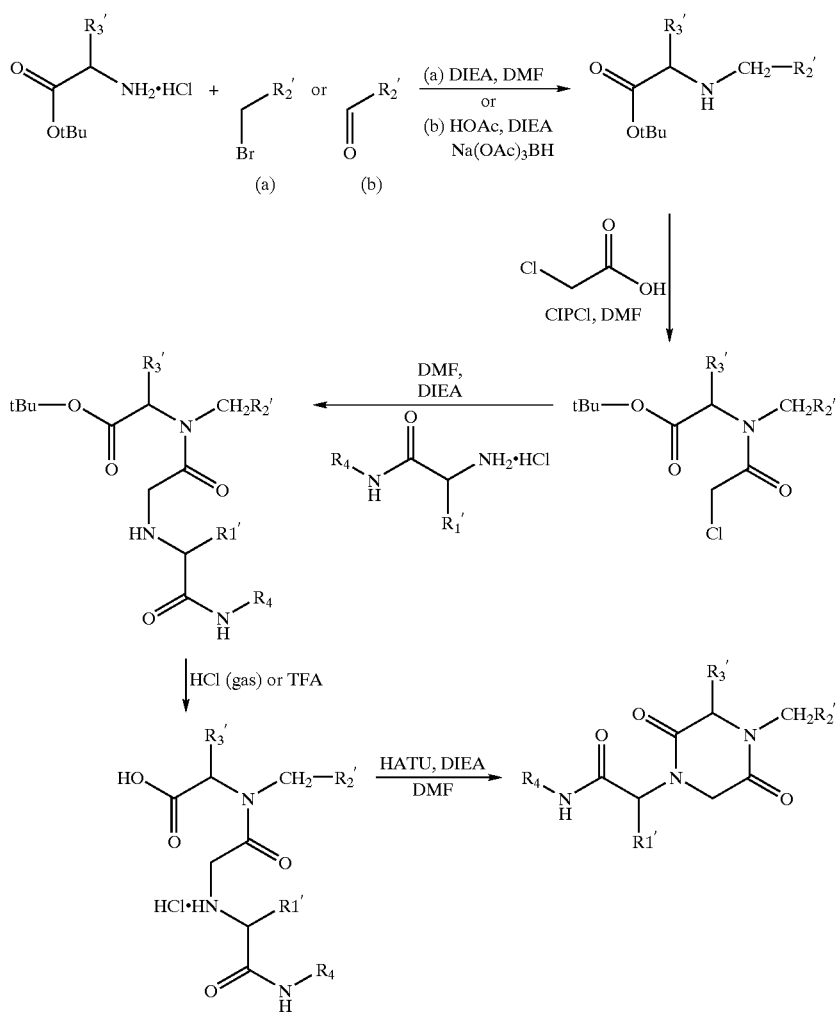
Further illustrative of the invention, the preparation of compounds of formula II wherein n is 2 can be carried out as illustrated below and in the examples herein.
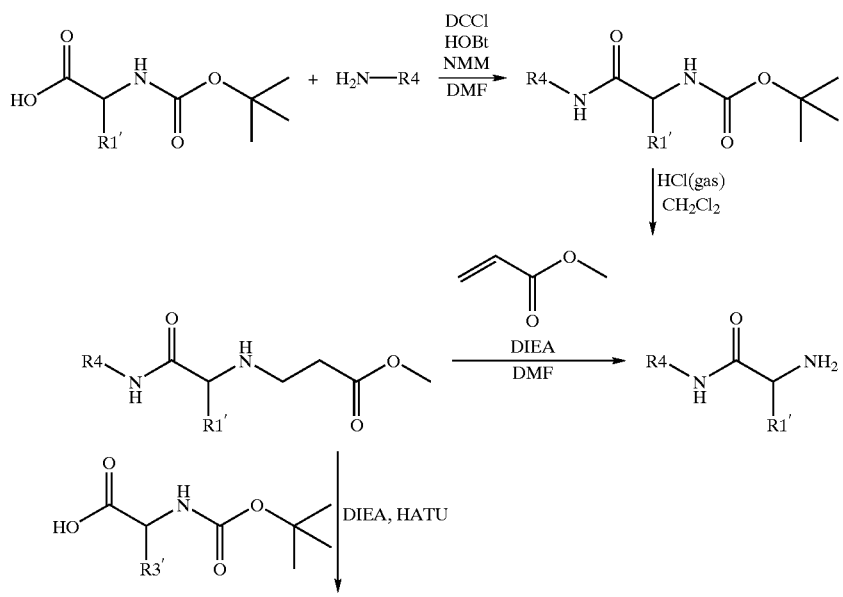

-continued

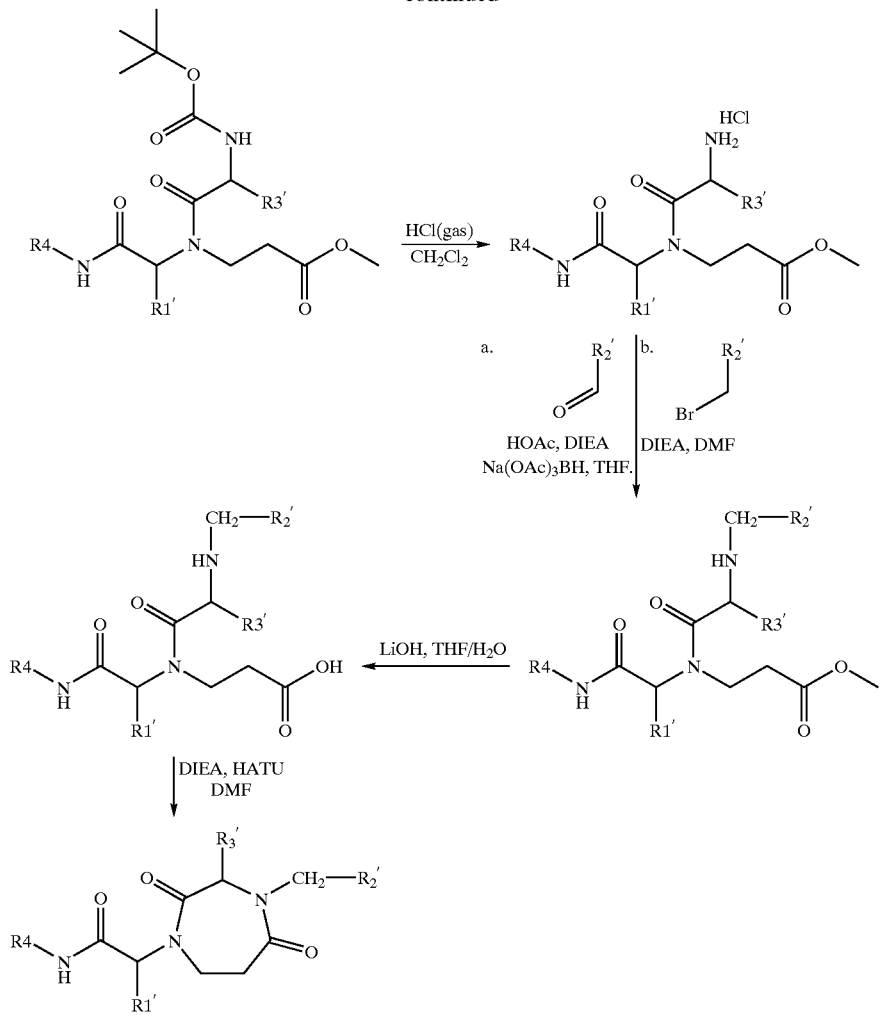

The preparation of corresponding compounds of compounds of formula IIa can be carried out according to the above synthetic schemes using starting materials with appropriate configurations at the asymmetric centers bearing the $R_1'$ and $R_3'$ substituents, e.g., as illustrated in the examples.

The compounds of the invention, in free form or in pharmaceutically acceptable salt form exhibit valuable pharmacological properties, e.g., as LFA-1 antagonists inhibiting LFA-1/ICAM-1, ICAM-2 or ICAM-3 interactions or inhibiting inflammation, e.g., as determined in in vitro and in vivo tests and are therefore indicated for therapy in the treatment of disorders responsive to LFA-1 inhibition.

The pharmacological properties can be demonstrated as follows:

A. In Vitro: Cell Free Assay

The assay measures the binding of soluble human ICAM-1 to immobilized human LFA-1. LFA-1 is purified from JY cells, a human lymphoblastoid B cell-line, by immunoaffinity chromatography as described by Dustin et al. (J. Immunol. 148, 2654–2663, 1992). ICAM-1 mouse Cκ fusion protein (ICAM-1) is produced using the baculovirus system as described by Weitz-Schmidt et al. (Anal. Biochem.238, 184–190, 1996).

Purified LFA-1 is diluted 1:20 in phosphate buffered saline (PBS) containing 2 mM $MgCl_2$, pH 7.4 and coated onto microtitre plates (Nunc) at 37° C. for 3 h. Plates are blocked with 1% heat-treated BSA in PBS for 2 hours at 37° C. followed by a washing step using PBS, 2 mM $MgCl_2$, 1% fetal calf serum, pH 7.4 (assay buffer). Compounds dissolved at 10 mM in DMSO are diluted in assay buffer and added to the plates. Biotinylated recombinant ICAM-1 in assay buffer (6 μg/ml) is added and allowed to bind at 37° C. for one hour. After incubation, wells are washed with assay buffer. Streptavidin-peroxidase diluted 1:5000 in assay buffer is added and incubated for 45 min at 37° C. Plates are then washed with assay buffer and 2,2'-azino-bis(3-ethylbenzothiazoline-6 sulfonic acid) diammonium salt substrate solution is added to each well. The reaction is stopped after 20 min and bound ICAM-1 is determined by measuring the optical density at 405 nm in a microplate reader.

In this assay, compounds of the invention inhibit adhesion of LFA-1 to ICAM-1. Compounds of Examples 1 and 4 have an $IC_{50}$ of about 30 nM and 23 nM, respectively, in this assay.

B. In Vivo Assays i) Murine Thioglycollate Induced Peritonitis

Thioglycollate is injected i.p. to mice and immediately thereafter the compound to be tested is given s.c. or p.o. The mice are sacrificed after 4 hours, the peritoneal cavity lavaged and total number of neutrophils in the lavage fluid is determined.

In this assay, the compounds of the invention inhibit thioglycollate induced neutrophil migration when administered s.c. or p.o. at a dose of about 0.01–100 mg/kg, either at the time of the thioglycollate injection or 3 hours before.

ii) Allergic Contact Dermatitis (ACD)

Groups of 8 female NMRI mice are sensitized on the shaved abdomen with 50 µl of oxazolone (Sigma, 2% in acetone) and challenged with 10 µl of 0.2 or 2.0% oxazolone on the inner surface of the right ear 7 days later. The low concentration of oxazolone for induction of the elicitation phase is used for testing compounds on systemic activity whereas the high concentration is applied for systemic testing. The unchallenged left ears serve as normal controls and dermatitis is evaluated from the individual differences in pinnal weight, which is taken as a measure of increase in inflammatory swelling 24 h after the challenge. Dermatitis is evaluated in test groups and for comparison in control groups. The test groups are treated with the test compounds either orally (twice, 2 h and immediately before challenge), subcutaneously (immediately before challenge) or topically (30 min after challenge at the site of elicitation of the ACD); the controls are treated similarly with the vehicles alone. For oral and subcutaneous administration the compounds are administered in an oil in water emulsion, for topical administration the compounds are administered in a mixture of ethanol, acetone and dimethylacetamide. The data of the test- and the vehicle-treated control groups are statistically analysed by ANOVA followed by Dunnet T-test (normal distribution or data) or by H and U-test, respectively. When administered p.o. at a dose of from about 0.1 to 20 mg/kg, compounds of the invention inhibit the elicitation phase of allergic contact dermatitis.

Antiinflammatory, antiarthritic and immunosuppressant activity can be determined according to tests well known in the art, e.g., in the carrageenan test, the antigen-induced arthritis test and experimental allergic encephalitis test.

iii) Rat Carrageenan Edema Model

Male OFA rats are treated orally with the compound to be tested or vehicle (saline). One to three hours later (0 hours) the rats receive a 100 µl intra-plantar injection of a 1% w/v carrageenan solution in 0.9% saline in the hind paw and the diameter of the paw is measured by means of a micro-calliper. The paw diameter measurements are repeated at times +3 and +5 hours after injection of the carrageenan. Percentage inhibition of paw swelling at 3 and 5 hours are calculated by reference to vehicle treated animals (0% inhibition).

Illustrative of the invention, the compound of example 1 inhibits paw swelling in the rat carrageenan edema model at a dose range of about 0.3 to 30 mg/kg p.o.

iv) Mouse Antigen-induced Arthritis Model

The test for rheumatoid arthritis is carried out by a modification of that described by Van de Loo et al., Arthritis Rheum. 1995; 35:164–172, e.g., as follows:

Female OFA-1 mice are sensitised intradermally on the back at two sites to methylated bovine serum albumin (mBSA) homogenised 1:1 with complete Freund's adjuvant on days −21 and −14 (0.1 ml containing 1 mg/ml mBSA). On day 0, the right knee receives 10 µl of 10 mg/ml mBSA in 5% glucose solution (antigen injected knee), while the left knee receives 10 µl of 5% glucose solution alone (vehicle injected knee). The diameters of the left and right knees are then measured using calipers immediately after the intra-articular injections and again on days 2, 4, 7, 9, 11 and 14. Compounds to be tested are administered once or twice daily by oral gavage; vehicle control (saline) is administered at 5 ml/kg. Right knee swelling is calculated as a ratio of left knee swelling, and the R/L knee swelling ratio plotted against time to give Area Under the Curve (AUC) graphs for control and treatment groups. The percentage inhibition of the individual treatment group AUCs are calculated vs the control group AUC (0% inhibition) using an Excel spread-sheet.

On day 14, the mice are sacrificed by $CO_2$ inhalation and the right and left knees removed and processed for undecalcified histology using a Histodur plastic embedding method (Leica AG, Germany). Sections (5 µm) from both the control and arthritic knees are cut on a RM 2165 rotation microtome (Leica AG, Germany). After staining, the slides are number coded as left knee/right knee pairs from each animal and scored in a blinded fashion for inflammatory cell infiltrate/hyperplasia, joint damage/erosions and cartilage proteoglycan loss.

Illustrative of the invention, the compound of example 1 inhibits knee swelling in the mouse antigen-induced arthritis model when administered at a dose range of about 0.3 to 30 mg/kg p.o., and also significantly reduces the histological damage to the knee.

The LFA-1 antagonists of the invention are, useful in the treatment and/or prevention of diseases or disorders mediated by LFA-1/ICAM-1, ICAM-2 or ICAM-3 interactions, e.g., ischemia/reperfusion injury, e.g., myocardial infarction, stroke, gut ischemia, renal failure or hemorrhagic shock, acute or chronic rejection of organ or tissue allo- or xenografts, infection diseases such as septic shock, adult respiratory distress syndrome, or traumatic shock. They are also useful in the treatment and/or prevention of acute or chronic inflammatory diseases or disorders or autoimmune diseases, e.g., rheumatoid arthritis, systemic lupus erythematosus, hashimoto's thyroidis, multiple sclerosis, myasthenia gravis, diabetes type I and uveitis, cutaneous manifestations of immunologically-mediated illnesses, inflammatory and hyperproliferative skin diseases (such as psoriasis, atopic dermatitis, alopecia aerata, allergic contact dermatitis, irritant contact dermatitis and further eczematous dermatitises, seborrhoeic dermatitis, lichen planus, pemphigus, bullous pemphigoid, epidermolysis bullosa, urticaria, angioedemas, vasculitides, erythema multiforme, cutaneous eosinophilias, lupus erythematosus, acne, granuloma annulare, pyoderma gangrenosum, sun burns or toxic epidermal necrolysis), inflammatory bowel disease, ophthalmic inflammatory diseases or immune-mediated conditions of the eye, such as auto-immune diseases, e.g., chronic keratitis, allergic conditions, e.g., vernal conjunctivitis, inflammatory conditions due to ocular surgery, e.g., keratoplasty. For the above uses the required dosage will of course vary depending on the mode of administration, the particular condition to be treated and the effect desired, in general, systemically at daily dosages of from about 0.1 to about 30 mg/kg body weight. An indicated daily dosage in the larger mammal is in the range from about 1 mg to about 200 mg, conveniently administered, e.g., in divided doses up to four times a day or in sustained release form.

For topical use, administration of a 1%–3% concentration of active substance several times daily, e.g., 2 to 5 times daily, can be used.

The compounds of the invention may be administered systemically or topically, by any conventional route, in particular enterally, e.g., orally, e.g., in the form of tablets or capsules, topically, e.g., in the form of lotions, gels, ointments or creams, or in a nasal or a suppository form. Percutaneous administration via patches or other delivery systems may also be a possible route for prevention or treatment of above diseases.

Pharmaceutical compositions comprising a compound of the invention in association with at least one pharmaceutical acceptable carrier or diluent may be manufactured in conventional manner by mixing with a pharmaceutically acceptable carrier or diluent. Unit dosage forms contain, for example, from about 1 mg to about 100 mg of active substance.

Topical administration is, e.g., to the skin. A further form of topical administration is to the eye.

The compounds of the invention may be administered in free form or in pharmaceutically acceptable salt form, e.g., as indicated above. Such salts may be prepared in conventional manner and exhibit the same order of activity as the free compounds.

In accordance with the foregoing the present invention further provides:

(a) a method of antagonizing LFA-1 and inhibiting LFA-1/ICAM-1, ICAM-2 or ICAM-3 binding in a mammal in need thereof which comprises administering to a said subject an effective amount of a compound of formula I, II, Ia or IIa as defined herein, or a pharmaceutically acceptable salt thereof;

(b) a method for preventing or treating disorders or diseases mediated by LFA-1/ICAM-1, ICAM-2 or ICAM-3 interactions, such as indicated above, e.g., rheumatoid arthritis, multiple sclerosis in a mammal in need of such treatment, which method comprises administering to said subject an effective amount of a compound of formula I, II Ia or IIa as defined herein, or a pharmaceutically acceptable salt thereof;

(c) a method for preventing or treating inflammatory diseases or disorders (acute or chronic) or autoimmune diseases, e.g., as indicated above, in a mammal in need of such treatment, which method comprises administering to said subject an effective amount of a compound of formula I, II, Ia or IIa as defined herein, or a pharmaceutically acceptable salt thereof;

(d) a method of treating arthritis, in particular rheumatoid arthritis, in a mammal in need of such treatment, which method comprises administering to said subject an effective amount of a compound of formula I, II, Ia or IIa as defined herein, or a pharmaceutically acceptable salt thereof;

(e) a method of treating inflammatory and hyperproliferative skin disorders such as psoriasis, eczema and dermatitis, in particular allergic dermatitis such as allergic contact dermatitis and atopic dermatitis, which method comprises administering to a mammal in need thereof an effective amount of a compound of formula I, II, Ia or IIa as defined herein, or a pharmaceutically acceptable salt thereof;

(f) a pharmaceutical composition for use in antagonizing LFA-1 activity comprising a compound of formula I, II, Ia or IIa as defined herein in free form or pharmaceutically acceptable salt form in association with a pharmaceutically acceptable diluent or carrier therefor.

The compounds of the invention may be administered as the sole active ingredient or together with other drugs in immunomodulating regimens or other anti-inflammatory agents for the treatment or prevention of allo- or xenograft acute or chronic rejection or inflammatory or autoimmune disorders. For example, they may be used in combination with cyclosporins, rapamycins or ascomycins, or their immunosuppressive analogs, e.g., cyclosporin A, cyclosporin G, FK-506, ABT-281, ASM 981, rapamycin, 40-O-(2-hydroxy)ethyl-rapamycin, etc.; corticosteroids; cyclophosphamide; azathioprene; methotrexate; FTY 720; leflunomide; mizoribine; mycophenolic acid; mycophenolate mofetil; 15-deoxyspergualine; immunosuppressive monoclonal antibodies, e.g., monoclonal antibodies to leukocyte receptors, e.g., MHC, CD2, CD3, CD4, CD7, CD25, CD28, B7, CD40, CD45, or CD58 or their ligands other immunomodulatory compounds, e.g., CTLA4Ig, or other adhesion molecule inhibitors, e.g., mAbs or low molecular weight inhibitors including Selectin antagonists and VLA-4 antagonists. For the treatment of arthritis, they can be used in combination, with, e.g., non-steroidal antiarthritic drugs, such as diclofenac, naproxen and ibuprofen, COX-2 inhibitors such as rofecoxib, celecoxib, etoricoxib, valdecoxib, parecoxib, tiracoxib, COX-189, and steroids such as dexamethasone, and other agents, such as methotrexate, gold salts, d-penicillamine and cyclosporin A.

Where the compounds of formula I are administered in conjunction with other immunosuppressive/immunomodulatory or anti-inflammatory therapy, e.g., for preventing or treating chronic rejection or arthritis as hereinabove specified, dosages of the co-administered immunosuppressant, immunomodulatory or anti-inflammatory compound will of course vary depending on the type of co-drug employed, e.g., whether it is a steroid or a cyclosporin, on the specific drug employed, on the condition being treated and so forth. In accordance with the foregoing the present invention provides in a yet further aspect:

(a) a method of use as defined above comprising co-administration, e.g., concomitantly or in sequence, of a therapeutically effective amount of a compound of formula I, Ia, II or IIa in free form or in pharmaceutically acceptable salt form, and a second drug substance, said second drug substance being an immunosuppressant, immunomodulatory or anti-inflammatory drug, e.g., as indicated above; and (b) a therapeutic combination, e.g., a kit, for use in any method of use as defined above, comprising a pharmaceutical composition containing a compound of formula I, II, Ia or IIa in free form or in pharmaceutically acceptable salt form, with at least one pharmaceutical composition comprising an immunosuppressant, immunomodulatory or anti-inflammatory drug. The kit may include instructions for its administration.

EXAMPLES

The following examples show representative compounds encompassed by this invention and their synthesis. However, it should be clearly understood that it is for purposes of illustration only.

Example 1

1H-1,4-Diazepine-1-acetamide, hexahydro-N-methyl-3-(2-methylpropyl)-α-[(2-naphthalenyl)methyl]-2,5-dioxo-4-[(3-quinolinyl)methyl]-, (αS, 3S)-

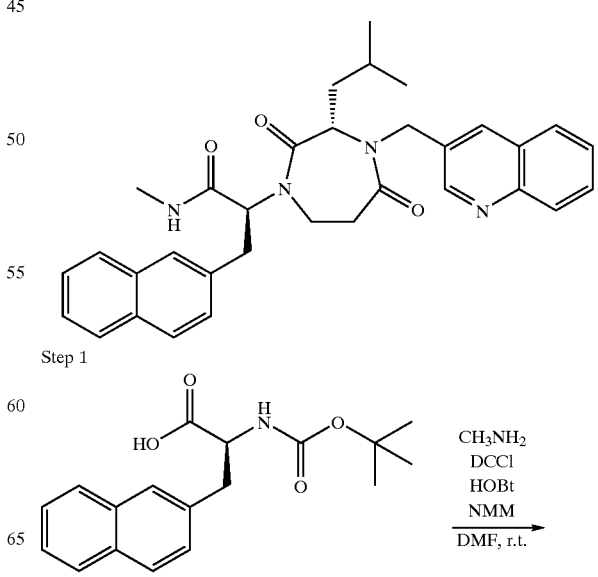

Step 1

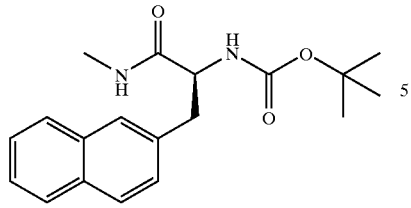

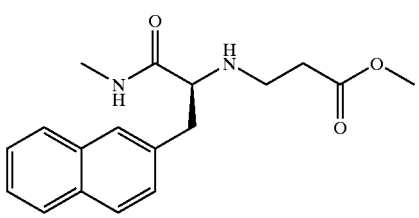

N-t Boc-L-3-(2-naphthyl)alanine (5.0 g, 15.85 mmol) is added to DMF (50 ml) at room temperature. 1-Hydroxybenzotriazole (HOBT) (4.29 g, 31.70 mmol) and 1,3-dicyclohexylcarbodiimide (DCCI) (9.81 g, 47.55 mmol) are added and the mixture is stirred for 5 min. 4-Methylmorpholine (NMM) (1.74 ml) and methylamine (16.0 ml) in THF are added and the mixture is stirred for 16 h. The white precipitate is collected and washed with DMF, (2×35 ml) and discarded. The remaining reaction mixture plus filtrates is added to 800 ml 5% NaHCO$_3$. The white resulting precipitate is collected and washed with 2×25 mls H$_2$O. The precipitate is dissolved in 100 ml CH$_2$Cl$_2$ and the mixture filtered to remove insoluble salts. The filtrate is washed with brine and dried over anhydrous magnesium sulfate. The solvent is then removed to give product as a white solid, mp: 161–165° C.

Product from step 2 (2.5 g, 9.44 mmol) is added to MeOH (50 ml) at room temperature. N,N-Diisopropylethylamine (DIEA) (3.28 ml, 18.9 mmol) is added and the mixture is stirred for 5 min. Methyl acrylate (1.5 ml) is then added and the mixture is stirred overnight. Additional methyl acrylate (0.6 ml) is added and the mixture stirred for a total of 48 h. The solvent is evaporated and the crude product is chromatographed using 1% MeOH in CH$_2$Cl$_2$ to give a white solid, mp: 92–94° C.

Step 2

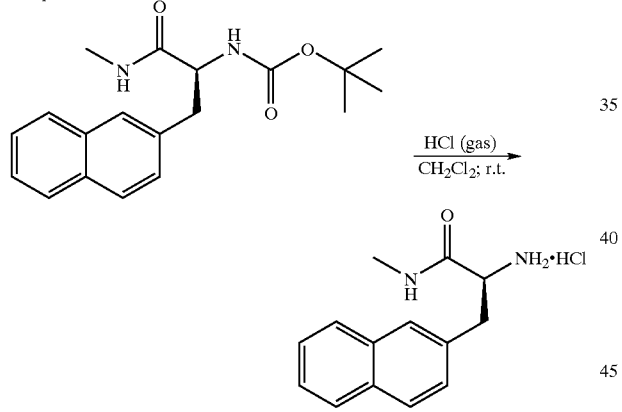

Step 4

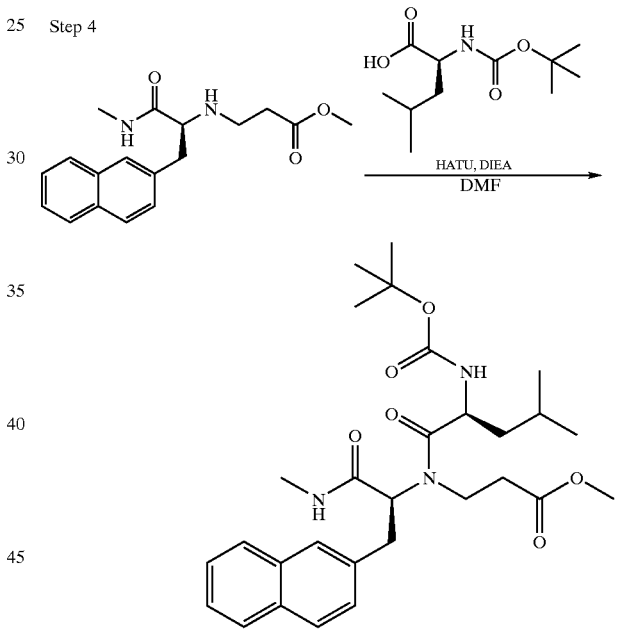

Product from step 1 (3.1 g, 9.44 mmol) is added to CH$_2$Cl$_2$ (60 ml). At room temperature (r.t.), anhydrous HCl gas is bubbled through the reaction mixture for 1 hour (h). The volume of the reaction mixture is reduced by half and the remainder is added to 100 ml diethyl ether with rapid agitation. A white solid forms, is filtered off, washed with 2×50 ml ether and dried to give the desired product, mp: 179–181° C.

Step 3

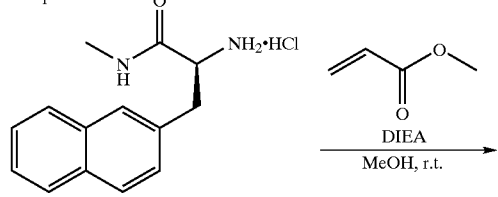

Product from step 3 (2.95 g, 9.38 mmol) is added to DMF (100 ml) at room temperature. N-t-Boc-L-leucine (2.2 g, 9.38 mmol) and DIEA (1.6 ml, 9.38 mmol) are added and the mixture is stirred for 5 min. The reaction is cooled to 0° C., [O-(7-azabenzotriazol-1-yl)-1,1,3,3-tetramethyluronium hexafluorophosphate] (HATU) (2.0 g, 9.38 mmol) is added and the reaction is allowed to warm to room temperature. After 24 h, the reaction is cooled to 0° C., N-t-Boc-L-leucine (4.3 g, 18.76 mmol), DIEA (3.3 ml) and HATU (7.6 g) are added. After a total of 48 h, solvent is removed and residue is dissolved in ethyl acetate. The solution is washed with 2×100 ml H$_2$O, 3×50 ml 5% NaHCO$_3$, 3×200 ml 10% Na$_2$CO$_3$ and dried. The solvent is removed and the residue chromatographed using 1.5% to 2% CH$_3$OH in CH$_2$Cl$_2$, obtaining product as a pale yellow foam, mp: 52–56° C.

Step 5

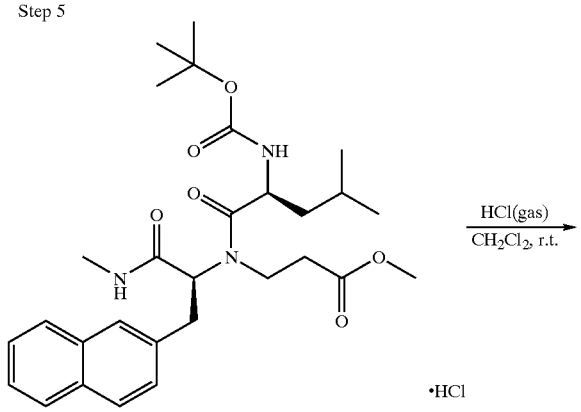

Product from step 4 (3.5 g, 6.63 mmol) is added to CH$_2$Cl$_2$ (100 ml) at room temperature. HCl gas is bubbled through the reaction mixture for 1 h. Part of the solvent (70 ml) is removed, and diethyl ether is added to form a white precipitate. The precipitate is filtered off, washed with ether and dried to give desired product, mp: 175–180° C. dec.

Step 6

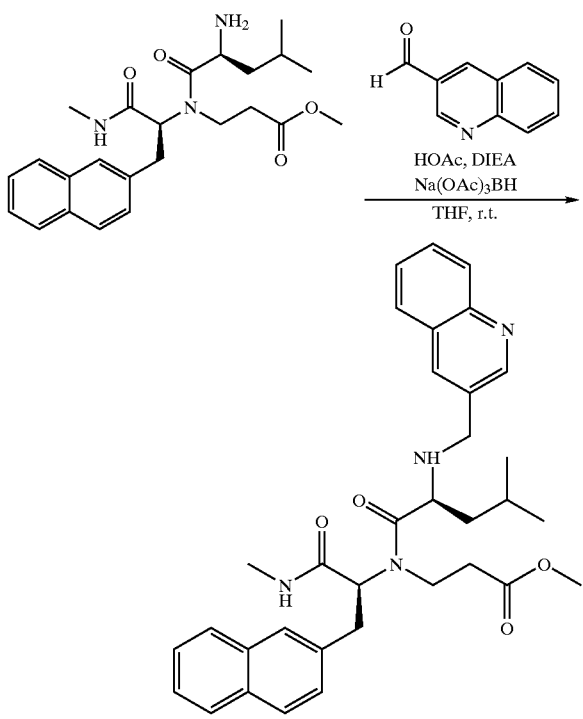

Product from step 5 (1.82 g, 3.92 mmol) is added to THF (40 ml) at room temperature. DIEA (0.7 ml, 3.92 mmol) is added, and the mixture is stirred for 10 min. Quinoline-3-carboxaldehyde (0.597 g, 3.80 mmol) is added, and the mixture stirred for 10 min. Sodium triacetoxyborohydride (1.25 g, 5.88 mmol) is added followed by acetic acid (2.0 ml). After 2 h, 100 ml saturated NaHCO$_3$ is added to the reaction mixture which is then extracted with diethyl ether. The ether extract is washed with brine, dried, and evaporated to dryness. The residue is chromatographed using 1% to 5% MeOH in CH$_2$Cl$_2$ to give the desired product as a white foam, mp: 48–54° C.

Step 7

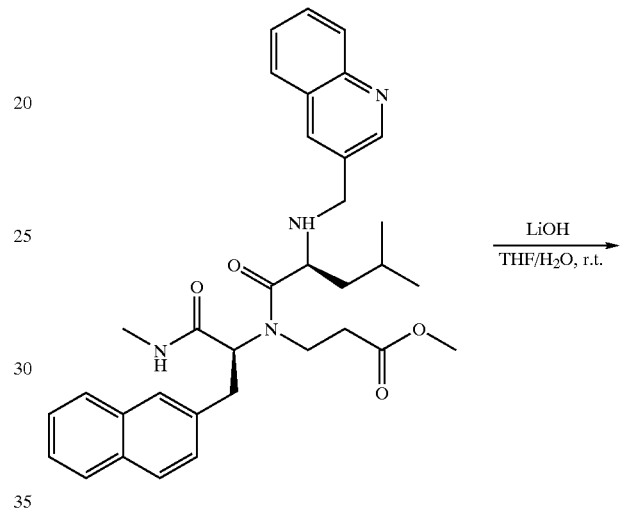

Product from step 6 (1.99 g, 3.50 mmol) is added to THF (15 ml) at room temperature. A solution of lithium hydroxide monohydrate (0.441 g, 10.5 mmol) in H$_2$O (5 ml) is added dropwise over 5 min. After 2 h, solvent is removed, residue is washed with 3×50 ml hexane and dissolved in H$_2$O. The solution is acidified with 1N HCl, neutralized with saturated NaHCO$_3$ and extracted with CH$_2$Cl$_2$. The extracts are dried and evaporated to dryness to give the desired product as a white foam, mp: 86–97° C.

Step 8

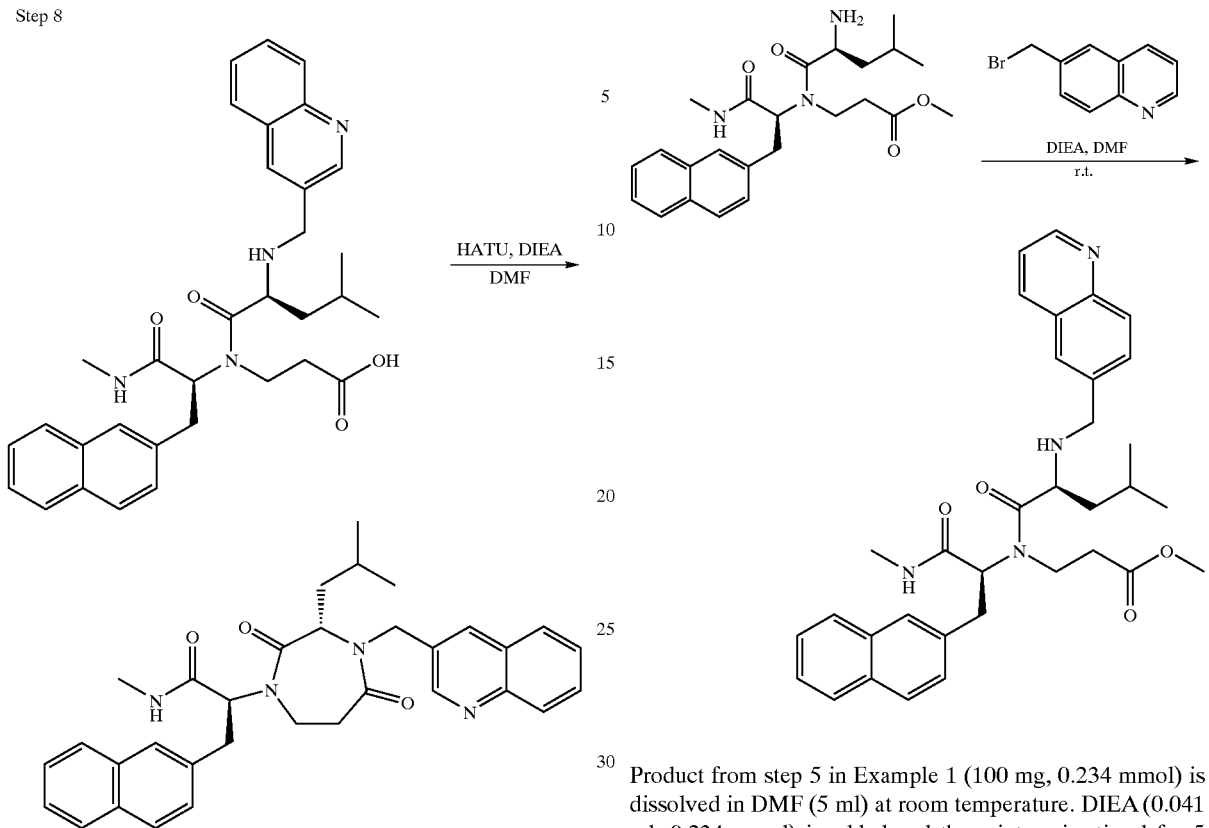

Product from step 7 (1.88 g, 3.39 mmol) is added to DMF (40 ml) at room temperature. DIEA (0.61 ml, 3.50 mmol) is added and the mixture is stirred for 5 min. The reaction mixture is cooled to 0° C. and HATU (1.33 g, 3.50 mmol) is added. After 1 h at 0° C., the solvent is removed, the residue is dissolved in CH$_2$Cl$_2$ and the solution washed with 1×200 ml H$_2$O, 1×150 ml brine, and dried. The solvent is removed and the residue is chromatographed using 1.5% to 3.5% MeOH in CH$_2$Cl$_2$, to give the desired title product, mp: 125–127° C.

Example 2

1H-1,4-Diazepine-1-acetamide, hexahydro-N-methyl-3-(2-methylpropyl)-α-[(2-naphthalenyl) methyl]-2,5-dioxo-4-[(6-quinolinyl)methyl]-, (αS, 3S)-

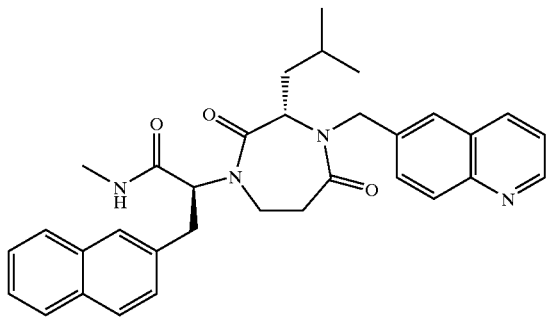

Product from step 5 in Example 1 (100 mg, 0.234 mmol) is dissolved in DMF (5 ml) at room temperature. DIEA (0.041 ml, 0.234 mmol) is added and the mixture is stirred for 5 min. 6-Bromomethylquinoline (52 mg, 0.234 mmol) is then added and the mixture is stirred for 48 h. Concentration and purification of the residue by chromatography using 2% to 3% MeOH in CH$_2$Cl$_2$ gives the desired intermediate as a white solid (MS: MH+569).

Further steps are carried out essentially as described in Example 1 to yield the title compound as a solid, mp: 102–105° C.

Example 3

1H-1,4-Diazepine-1-acetamide, 4-[(4-bromophenyl) methyl]hexahydro-N-methyl-3-(2-methylpropyl)-α-[(2-naphthalenyl)methyl]-2,5-dioxo-, αS,3S)-

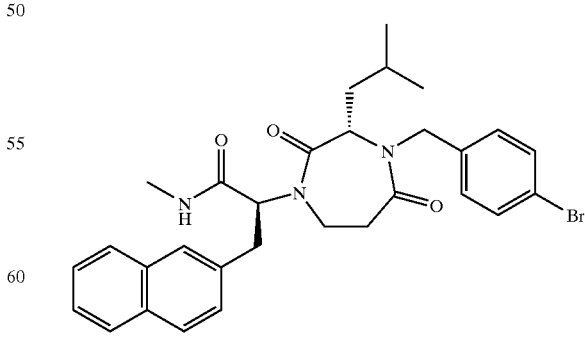

The title compound is prepared following essentially the procedures of Example 2. The product is isolated as a solid, mp: 105–108° C.

Example 4

1H-1,4-Diazepine-1-acetamide, hexahydro-N-methyl-3-(2-methylpropyl)-α-[(2-naphthalenyl)methyl]-2,5-dioxo-4-[3-(4-pyridinyl)-2-propenyl]-, αS,3S)-

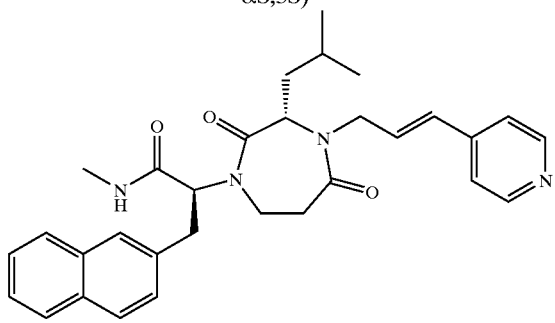

The title compound is prepared using essentially the procedures of Example 1. The product is isolated as a solid, mp: 68–72° C.

Example 5

1H-1,4-Diazepine-1-acetamide, 4-[(4-dimethylaminophenyl)methyl]hexahydro-N-methyl-3-(2-methylpropyl)-α-[(2-naphthalenyl)methyl]-2,5-dioxo-, αS,3S)-

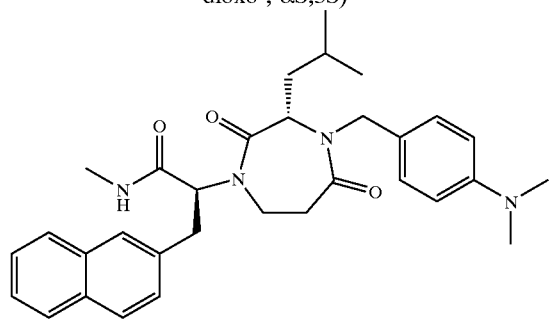

The title compound is prepared following essentially the procedures of Example 1. The product is isolated as a solid, mp: 92–94° C.

Example 6

1H-1,4-Diazepine-1,4-diacetamide, hexahydro-$N^1$-methyl-3-(2-methylpropyl)-α-[(2-naphthalenyl)methyl]-2,5-dioxo-$N^4$-(4-pyridinyl)]-, αS,3S)-

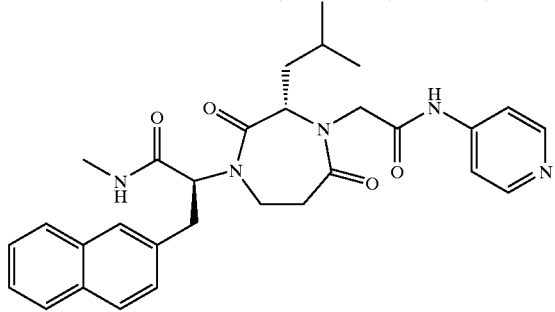

The title compound is prepared following essentially the procedures of Example 2. The product is isolated as foam, mp: MS(ESI): MH+530.

Example 7

1H-1,4-Diazepine-1-acetamide, hexahydro-4-[(4-hydroxy-3-methoxyphenyl)methyl]-N-methyl-3-(2-methylpropyl)-α-[(2-naphthalenyl)methyl]-2,5-dioxo-, αS,3S)-

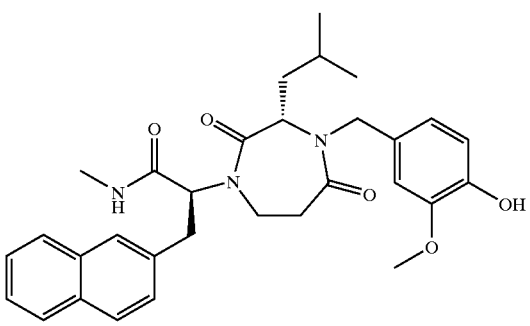

The title compound is prepared following essentially the procedures of Example 1. The product is isolated as a solid, mp: 67–69° C.

Examples 8–13

The following compounds are prepared according to the methods previously described.

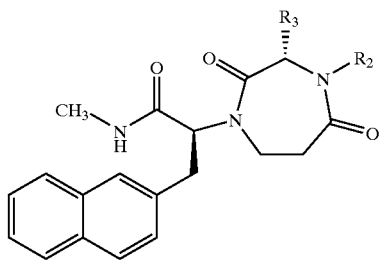

| Example | $R_2$ | $R_3$ | m.p. (° C.) or MH+ |
|---|---|---|---|
| 8 | 4-hydroxy-3-methoxybenzyl | —CH$_2$CONHCH$_3$ | MH+ = 547 |
| 9 | 3-quinolinylethyl | 2-methylpropyl | 60–67 |
| 10 | benzyl | 2-methylpropyl | 57–62 |
| 11 | 3-benzyloxybenzyl | 2-methylpropyl | 57–63 |
| 12 | 3-hydroxybenzyl | 2-methylpropyl | 78–82 |
| 13 | 4-pyridylmethyl | 2-methylpropyl | 63–70 |

Example 14

1H-1,4-Diazepine-1-acetamide, hexahydro-N-methyl-3-(2-methylpropyl)-α-[(2-naphthalenyl)methyl]-2,5-dioxo-4-[(3-quinolinyl)methyl]-, αR, 3R)-

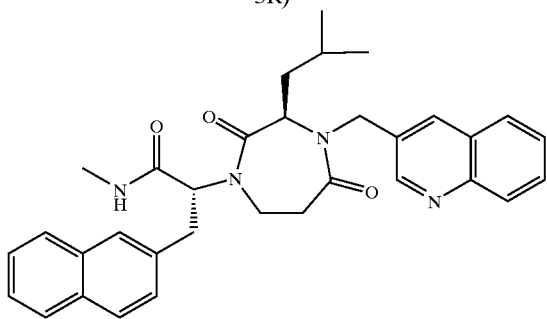

The title compound is prepared essentially as described in Example 2. The product is isolated as a solid, mp: 43–54° C.

Example 15

1H-1,4-Diazepine-1-acetamide, hexahydro-N-methyl-3-(2-methylpropyl)-α-[(2-naphthalenyl)methyl]-2,5-dioxo-4-[(3-quinolinyl)methyl]-, αS, 3R)-

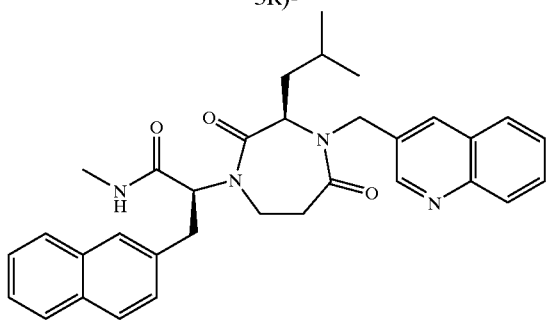

The title compound is prepared essentially as described in Example 2. The product is isolated as a solid, mp: 53–59° C.

Example 16

1H-1,4-Diazepine-1-acetamide, hexahydro-N-methyl-3-(2-methylpropyl)-α-[(2-naphthalenyl)methyl]-2,5-dioxo-4-[(3-quinolinyl)methyl]-, (αR, 3S)-

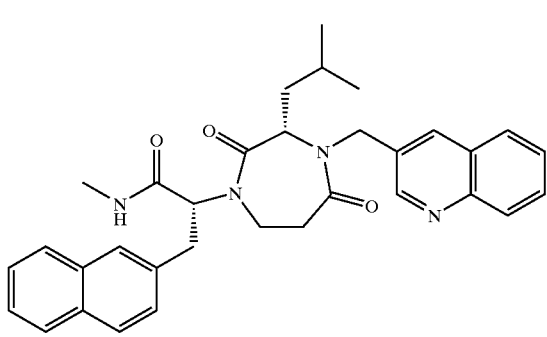

The title compound is prepared essentially as described in Example 2. The product is isolated as a solid; mp: 38–44° C.

Example 17

1-Piperazineacetamide, hexahydro-N-methyl-3-(2-methylpropyl)-α-[(2-naphthalenyl)methyl]-2,5-dioxo-4-[(6-quinolinyl)methyl]-, αS,3S)-

Step 1

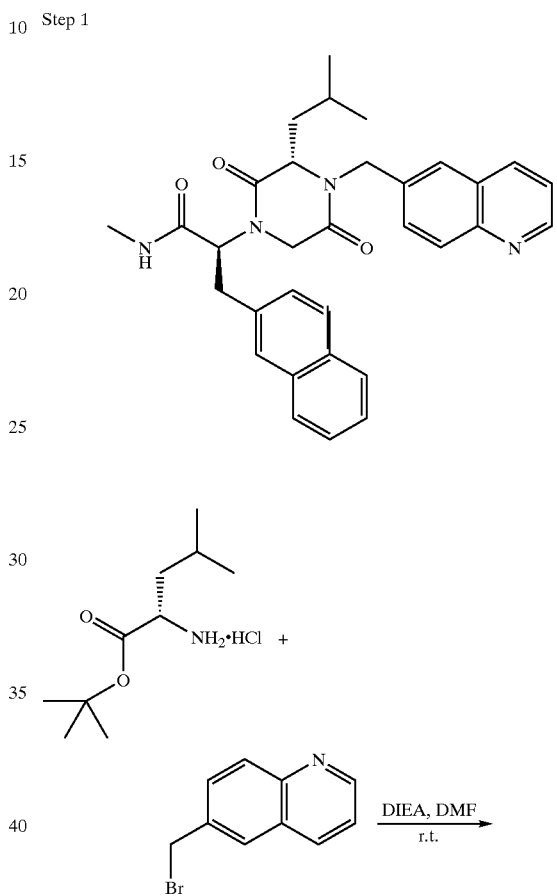

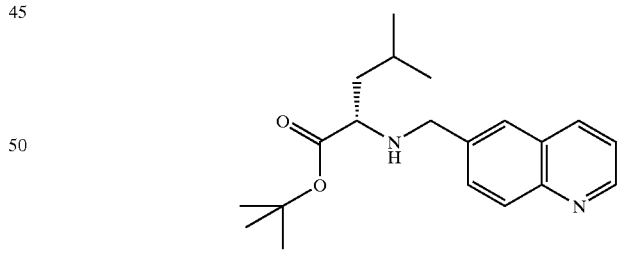

L-leucine t-butyl ester hydrochloride (287 mg, 1.3 mmol) is dissolved in DMF (4 ml), and DIEA (0.475 ml, 2.1 mmol) is added dropwise. A solution of 4-bromomethylquinoline (200 mg, 0.9 mmol) in DMF (4 ml) is added dropwise, the mixture is stirred for 16 h at rt, concentrated to dryness and chromatographed using 2% $CH_3OH/CH_2Cl_2$ to give a yellow oil.

Step 2

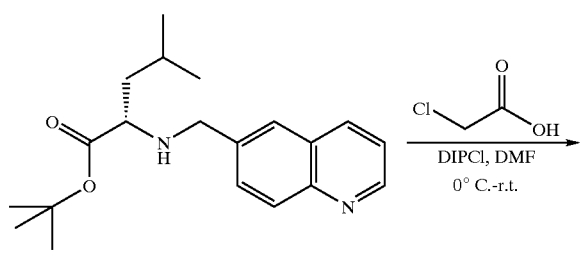

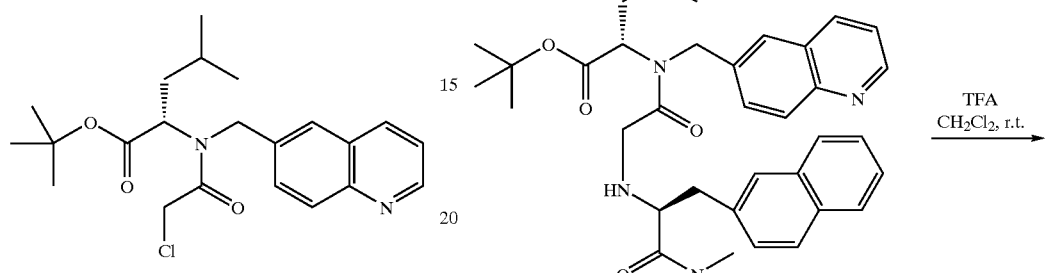

To a solution of product from step 1 (40 mg, 0.12 mmol) in DMF (2 ml) at 0° C. is added dropwise a premixed solution of chloroacetic acid (19.6 mg, 0.21 mmol) and diisopropylcarbodiimide (DIPCI) (0.034 ml, 0.22 mmol) in DMF (1 ml). The reaction mixture is stirred and allowed to reach room temperature. After 2 h, the reaction mixture is added to brine, the mixture is extracted with ethyl acetate, the extract is dried and concentrated to dryness. The crude product is used directly in the next step.

Step 3

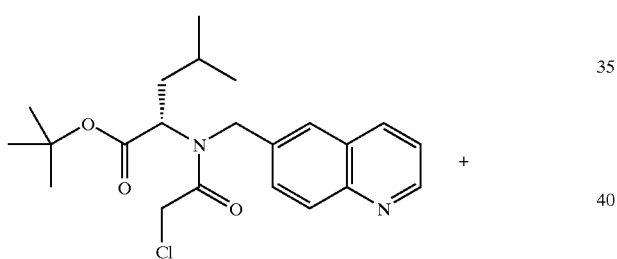

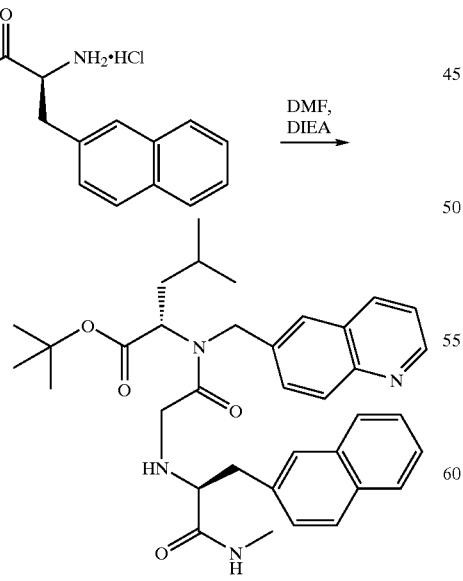

Crude product from step 2 (0.12 mmol) is dissolved in DMF (3 ml). L-3-(2-naphthyl)alanine N-methylamide (the free base of product from step 2 of example 1) (35 mg, 0.12 mmol) is added followed by DIEA (0.031 ml, 0.18 mmol). The reaction mixture is stirred at 40° C. for 16 h and then at 70° C. for 2 h, concentrated to dryness and chromatographed using 7% CH₃OH/CH₂Cl₂ to obtain crude product of above structure.

Step 4

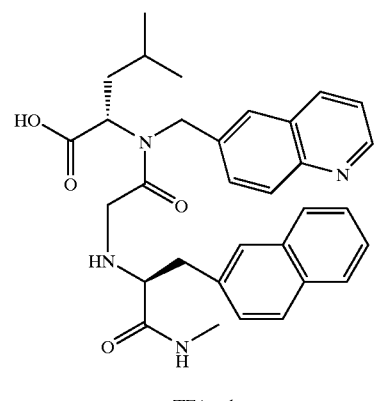

TFA salt

To a solution of product from step 3 (25.8 mg, 0.043 mmol) in CH₂Cl₂ (3 ml) at rt is added TFA (0.8 ml). After 3 h, the reaction mixture is concentrated and the crude product is used directly in the next step.

Step 5

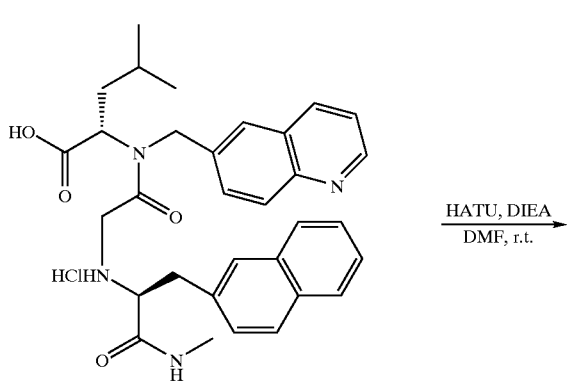

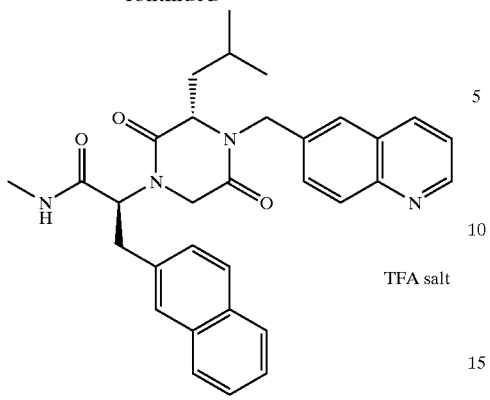

TFA salt

To a solution of the crude product from step 4 (0.043 mmol) in DMF (2 ml) is added DIEA (0.03 ml, 0.172 mmol) or enough to render the solution basic. The solution is cooled to 0° C. and HATU (17 mg, 0.044 mmol) is added. The reaction mixture is stirred at rt for 4 h, concentrated to dryness and purified by reverse phase chromatography (CH$_3$CN and 0.1% TFA/water) to give product as TFA salt, mp: 98–102° C.

Example 18

1-Piperazineacetamide, 4-[(4-bromophenyl)methyl] hexahydro-N-methyl-3-(2-methylpropyl)-α-[(2-naphthalenyl)methyl]-2,5-dioxo-, αS,3S)-

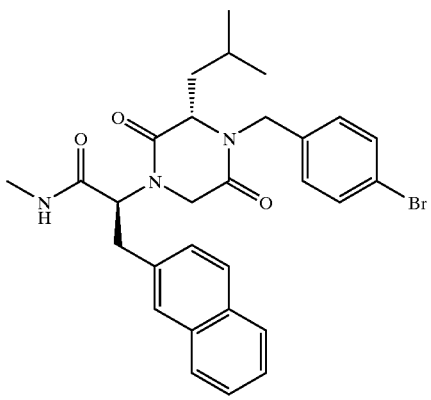

The title compound is prepared following essentially the procedures of Example 17. The product is isolated as a solid, mp: 107–111° C.

Example 19

1-Piperazineacetamide, hexahydro-N-methyl-3-(2-methylpropyl)-α-[(2-naphthalenyl)methyl]-2,5-dioxo-4-[4-[(3-pyridinyl)phenyl]methyl]-, (αS,3S)-

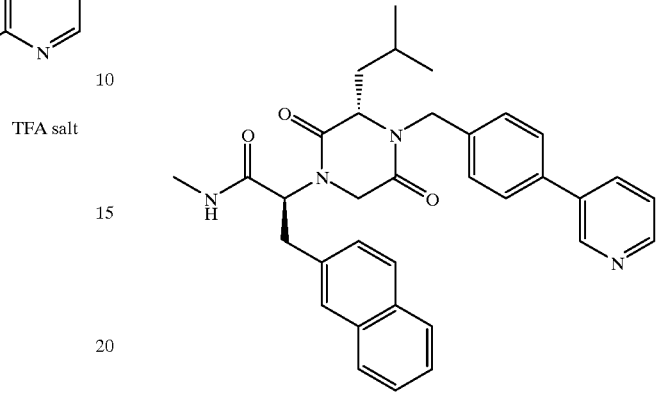

The title compound is prepared from Example 18 by Stille coupling with 3-(tri-n-butylstannyl)pyridine using a reported procedure (S. Wattanasin, *Synth. Commn.*, 18, 1919, 1988). The product is isolated as solid, mp: 50–53° C.

What is claimed is:

1. A compound of the formula I

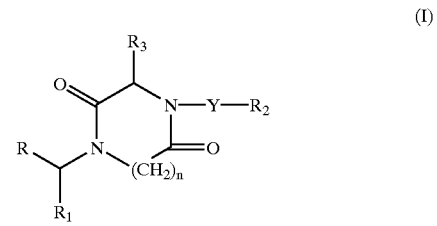

(I)

wherein R is carboxy, esterified carboxy or amidated carboxy;

$R_1$ and $R_3$ are independently lower alkyl, (hydroxy, lower alkoxy, amino, acylamino, mono- or di-lower alkylamino or mercapto)-lower alkyl, lower alkyl-(thio, sulfinyl or sulfonyl)-lower alkyl, cycloalkyl, aryl, biaryl, (cycloalkyl, aryl or biaryl)-lower alkyl, or (carboxy, esterified carboxy or amidated carboxy)-lower alkyl;

$R_2$ is hydrogen, lower alkyl, cycloalkyl, aryl, biaryl, arylaminocarbonyl, or aryl-(oxy, thio or amino);

n is 1 or 2;

Y is lower-alkylene or lower alkenylene;

or a pharmaceutically acceptable salt thereof; and
  wherein in the above definitions,
    aryl represents carbocylic or heterocyclic aryl;
    heterocyclic aryl represents monocyclic or bicyclic heterocyclic aryl;
    monocyclic heterocyclic aryl represents optionally substituted thiazolyl, thienyl, furanyl or pyridyl;
    optionally substituted thiazolyl represents thiazolyl or thiazolyl substituted by lower alkyl;
    optionally substituted thienyl represents thienyl or thienyl substituted by lower alkyl;

optionally substituted furanyl represents furanyl or furanyl substituted by lower alkyl;
optionally substituted pyridyl represents pyridyl or pyridyl substituted by lower alkyl, halogen or cyano;
bicyclic heterocyclic aryl represents optionally substituted quinolinyl, isoquinolinyl, indolyl or benzothiazolyl;
optionally substituted quinolinyl represents quinolinyl or quinolinyl substituted by hydroxy, lower alkyl, lower alkoxy or halogen;
optionally substituted isoquinolinyl represents isoquinolinyl or isoquinolinyl substituted by hydroxy, lower alkyl, lower alkoxy or halogen;
optionally substituted indolyl represents indolyl, indolyl substituted on carbon by hydroxy, lower alkyl, lower alkoxy or halogen, or indolyl substituted on nitrogen by lower alkyl or aryl-lower alkyl;
optionally substituted benzothiazolyl represents benzothiazolyl or benzothiazolyl substituted by hydroxy, lower alkyl, lower alkoxy or halogen;
biaryl represents phenyl substituted by carbocyclic or heterocyclic aryl;
esterified carboxy represents carboxy esterified in form of a pharmaceutically acceptable ester selected from a lower alkyl ester, a cycloalkyl ester, a lower alkenyl ester, a benzyl ester and a mono- or di-substituted lower alkyl ester; and
a mono- or di-substituted lower alkyl ester represents an ω-(amino, mono- or di-lower alkylamino, carboxy, lower alkoxycarbonyl)-lower alkyl ester or an α-(lower alkanoyloxy, lower alkoxycarbonyl or di-lower alkylaminocarbonyl)-lower alkyl ester; or
amidated carboxy represents carboxy derivatized in form of a pharmaceutically acceptable amide selected from the unsubstituted amide, an N-mono-lower alkyl amide, an N,N-di-lower alkylamide and an amide of a cyclic amine.

2. A compound according to claim 1 wherein n is 2.

3. A compound according to claim 2 wherein R is carboxy derivatized in form of a pharmaceutically acceptable amide; $R_1$ is aryl-lower alkyl; $R_2$ is aryl; $R_3$ is lower alkyl, aryl, or cycloalkyl-lower alkyl; and Y is $C_1$–$C_4$-alkylene or $C_2$–$C_4$-alkenylene; or a pharmaceutically acceptable salt thereof.

4. A compound according to claim 1 of the formula II

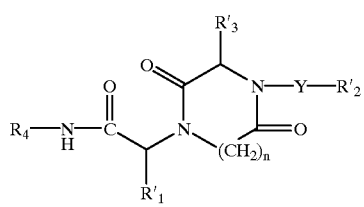

(II)

wherein $R_1'$ is bicyclic aryl-lower alkyl; $R_2'$ is bicyclic aryl; $R_3'$ is monocyclic aryl or lower alkyl; $R_4$ is hydrogen or lower alkyl; n is 1 or 2; Y is $C_{1-4}$-alkylene; or a pharmaceutically acceptable salt thereof.

5. A compound according to claim 4 of formula II wherein $R_1'$ is naphthyl-lower alkyl or quinolinyl-lower alkyl; $R_2'$ is quinolinyl; Y is methylene; and n is 2; or pharmaceutically acceptable salt thereof.

6. A compound according to claim 1 the formula Ia

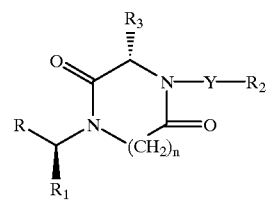

(Ia)

wherein n, Y, R, $R_1$, $R_2$ and $R_3$ have meaning as defined in said claim; or a pharmaceutically acceptable salt thereof.

7. A compound according to claim 4 of the formula IIa

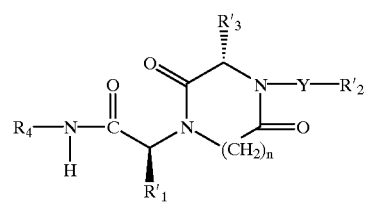

(IIa)

wherein n, Y, $R_1'$, $R_2'$, $R_3'$ and $R_4$ have meaning as defined in said claim; or a pharmaceutically acceptable salt thereof.

8. A compound according to claim 7 of formula IIa, wherein $R_1$ is 2-naphthylmethyl; $R_2'$ is 3-quinolinyl; $R_3'$ is isobutyl; $R_4$ is methyl; Y is $CH_2$; and n is 2; or a pharmaceutically acceptable salt thereof.

9. A process for the preparation of a compound according to claim 1 of formula I which process comprises:

(a) cyclizing a compound of formula III

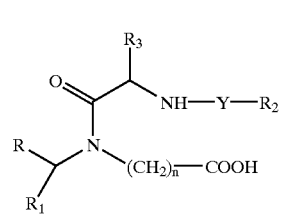

(III)

or a reactive functional derivative thereof, wherein R, $R_1$–$R_3$, Y and n have meaning as defined in claim 1; or (b) cyclizing a compound of formula IV

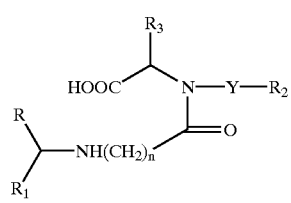

(IV)

or a reactive functional derivative thereof, wherein R, $R_1$–$R_3$, Y and n have meaning as defined in claim 1;
and if desired converting the resulting compound of formula I into a pharmaceutically acceptable salt thereof.

10. A pharmaceutical composition comprising a compound according to claim 1 in combination with a pharmaceutically acceptable carrier.

11. A method of treating arthritis in mammals which comprises administering to a mammal in need thereof an effective amount of a compound according to claim 1.

12. A method according to claim 11 of treating rheumatoid arthritis.

13. A method of treating hyperproliferative and inflammatory skin disorders in mammals which comprises administering to a mammal in need thereof an effective amount of a compound according to claim 1.

14. A method according to claim 13 of treating psoriasis, eczema and dermatitis.

15. A method according to claim 13 of treating allergic contact dermatitis and atopic dermatitis.

16. A compound according to claim 4 wherein n is 2.

17. A method of treating disorders or diseases mediated by LFA-1/ICAM-1, ICAM-2 or ICAM-3 interactions selected from transplant rejection, chronic inflammation, psoriasis, eczema/dermatitis, asthma and arthritis, in a mammal in need of such treatment which comprises administering to said subject an effective amount of a compound according to claim 1.

\* \* \* \* \*